United States Patent [19]
Alpenfels et al.

[11] Patent Number: 5,753,095
[45] Date of Patent: May 19, 1998

[54] PLASTIC MOLD FOR ELECTROPHORESIS GEL

[75] Inventors: William F. Alpenfels, Del Mar; Sheldon Engelhorn, Encinitas; David Manis, Del Mar, all of Calif.

[73] Assignee: Novel Experimental Technology, San Diego, Calif.

[21] Appl. No.: 716,680

[22] Filed: Sep. 16, 1996

Related U.S. Application Data

[63] Continuation of Ser. No. 308,837, Sep. 19, 1994, abandoned.

[51] Int. Cl.⁶ .................................................. G01N 27/26
[52] U.S. Cl. ........................ 204/616; 204/615; 204/470; 204/465; 204/620
[58] Field of Search .................................. 204/456, 465, 204/470, 606, 613, 616, 619, 620

[56] References Cited

U.S. PATENT DOCUMENTS

| | | | |
|---|---|---|---|
| 3,442,686 | 5/1969 | Jones | 117/70 |
| 4,548,869 | 10/1985 | Ogawa et al. | 428/474.7 |
| 4,548,870 | 10/1985 | Ogawa et al. | 428/474.7 |
| 4,579,783 | 4/1986 | Ogawa et al. | 428/475.2 |
| 4,600,641 | 7/1986 | Ogawa et al. | 428/355 |
| 4,718,998 | 1/1988 | Ogawa et al. | 204/299 |
| 4,722,777 | 2/1988 | Ogawa et al. | 204/299 |
| 4,737,258 | 4/1988 | Ogawa et al. | 204/299 |
| 4,737,259 | 4/1988 | Ogawa et al. | 204/299 |
| 4,810,341 | 3/1989 | Tezuka et al. | 204/182.8 |
| 4,820,398 | 4/1989 | Yamamoto | 204/299 |
| 4,861,411 | 8/1989 | Tezuka | 156/344 |
| 4,897,306 | 1/1990 | Sugimoto et al. | 204/182.8 |
| 4,954,236 | 9/1990 | Kushner et al. | 204/299 R |
| 5,084,356 | 1/1992 | Deak et al. | 428/458 |
| 5,085,904 | 2/1992 | Deak et al. | 428/35.7 |
| 5,224,441 | 7/1993 | Felts et al. | 118/718 |
| 5,364,665 | 11/1994 | Felts et al. | 427/571 |

FOREIGN PATENT DOCUMENTS

| | | | |
|---|---|---|---|
| 0 299 754 A2 | 7/1988 | European Pat. Off. | C23C 16/40 |
| 0 490 729 A1 | 6/1992 | European Pat. Off. | |
| 62-247244 | 10/1987 | Japan . | |
| 62-284253 | 12/1987 | Japan . | |
| 24768 | 6/1994 | Japan . | |
| WO 90/13020 | 11/1990 | WIPO | G01N 27/26 |
| WO 92/14538 | 9/1992 | WIPO . | |
| wO 94/08701 | 4/1994 | WIPO . | |

OTHER PUBLICATIONS

A. Andrews, Electrophoresis, pp. 5–24 (2nd ed. Oxford University Press, 1986) No Month Available.

J. Felts, Transparent Gas Barrier Technologies (Airco Coating Technology) No Month Available.

FMC, Bioproducts Catalog 1993, pp. 42–44 (1993) No Month Available.

B. Hames and D. Rickwood, Gel Electrophoresis of Proteins, pp. 1–50 (2d ed. Oxford University Press, 1990) No Month Available.

Pharmacia, Pharmacia LKB Biotechnology Products Catalog 1992, pp. 189, 191 (1992) No Month Available.

A. Rizika, Vapor Coating with SiOx: The Flexible Glass Barrier (Presented at Pack Expo '92 Conference, Chicago, Nov. 8–11, 1992) (Airco Coating Technology) No Month Available.

Serva, Specialty Products Catalog 1992/93, pp. 209, 214, 258 (1992) No Month Available.

WPIDS and JAPIO abstracts of JP62284253 (Takeshi et al.) Dec. 10, 1987.

(List continued on next page.)

*Primary Examiner*—Bruce F. Bell
*Assistant Examiner*—Alex Noguerda
*Attorney, Agent, or Firm*—Fish & Neave

[57] ABSTRACT

An improved plastic mold for the polymerization of electrophoresis gels. The improved electrophoresis gel mold comprises non-conductive plastic film. The film is supported by a rigid plastic frame. The frame maintains the integrity of the electrophoresis gel. The molds of the present invention are particularly useful in the manufacture of precast electrophoresis gels.

17 Claims, 2 Drawing Sheets

OTHER PUBLICATIONS

A. Rizika (Vapor Coating with SiOx: The Flexible Glas BArrier, presented at Pack Expo '92 Conference, Chicago, Nov. 8–11, 1992).

B. J. Radola (Electrophoresis '79, Ultrathin–layer Isoelectric Focusing in 50–100 um Polyacrylamide Gels in Silanized Glass Plates or Polyester Films, B. J. Radola ed., Walter de Gruyter publ., 79–94), 1980.

PLASTIC MOLD FOR ELECTROPHORESIS GEL

This is a continuation of application Ser. No. 08/308,837, filed Sep. 19, 1994 entitled Plastic Mold For Electrophoresis Gel, now abandoned.

This invention relates to gel electrophoresis. More particularly, this invention relates to a novel gel mold for casting electrophoresis gels.

BACKGROUND OF THE INVENTION

Gel electrophoresis is a common procedure for the separation of biological molecules, such as DNA, RNA, polypeptides and proteins. In gel electrophoresis, the molecules are separated into bands according to the rate at which an imposed electric field causes them to migrate through a filtering gel.

The gel used in the electrophoresis process has an open molecular network structure, defining pores which are saturated with an electrically conductive buffered solution of a salt. These pores are large enough to admit passage of the migrating macromolecules through the gel.

During the electrophoresis process, the gel is placed in a chamber in contact with buffer solutions which make electrical contact between the gel and the cathode or anode of an electrical power supply. A sample containing the macromolecules and a tracking dye is placed on top of the gel. An electric potential is applied to the gel causing the sample macromolecules and tracking dye to migrate toward the bottom of the gel. The electrophoresis is halted just before the tracking dye reaches the end of the gel. The locations of the bands of separated macromolecules are then determined. By comparing the distance moved by particular bands in comparison to the tracking dye and macromolecules of known mobility, the mobility of other macromolecules can be determined. The size of the macromolecule can then be calculated.

The rate of migration of macromolecules through the gel depends upon three principle factors: the porosity of the gel; the size and shape of the macromolecule; and the charge density of the macromolecule. It is critical to an effective electrophoresis system that these three factors be uniform within a particular gel and reproducible from gel to gel and from sample to sample. However, maintaining uniformity is difficult because each of these factors is sensitive to many variables in the chemistry of the gel system.

Polyacrylamide gels are commonly used for electrophoresis. Other gels suitable for electrophoresis include agarose gels and starch gels. Polyacrylamide gel electrophoresis or PAGE is popular because the gels are optically transparent, electrically neutral and can be made with a range of pore sizes.

The porosity of a polyacrylamide gel is in part defined by the total percentage of acrylamide monomer plus crosslinker monomer ("% T") it contains. The greater the concentration, the less space there is between strands of the polyacrylamide matrix and hence the smaller the pores through the gel. An 8% polyacrylamide gel has larger pores than a 12% polyacrylamide gel. An 8% polyacrylamide gel consequently permits faster migration of macromolecules with a given shape, size and charge density. When smaller macromolecules are to be separated, it is generally preferable to use a gel with a smaller pore size such as a 20% gel. Conversely, for separation of larger macromolecules, a gel with a larger pore size is often used, such as an 8% gel.

Pore size is also dependent upon the amount of crosslinker used to polymerize the gel. At any given total monomer concentration, the minimum pore size for a polyacrylamide gel is obtained when the ratio of total monomer to crosslinker is about 20:1, (the common expression for this ratio would be "5% C").

The basic apparatus used in this electrophoresis technique consists of a gel enclosed in a mold. Although the configuration of the mold can vary, there are two basic gel electrophoresis mold configurations, rod gel electrophoresis and slab gel electrophoresis. In rod gel electrophoresis, the mold typically consists of a tube. In slab gel electrophoresis, the gel mold typically consists of two non-conducting glass or plastic plates which serve to support the gel.

In slab gel electrophoresis, the two flat plates are made of either glass or plastic. In either glass or plastic molds, the plates are separated by spacers along two longitudinal edges with the transverse edges remaining open. The spacers separate the plates by a predetermined distance and allow for the gel to fit in between the plates. The spacer also serves to seal the gel from ambient conditions. The plates are commonly held together by clamping, taping, or gluing. Plastic plates can also be held together by ultrasonic welding.

During the gel casting process, the mold is commonly placed in a casting stand in which the bottom edge of the mold is pressed against a surface that forms a seal with the bottom of the mold. The gel solution is then poured into the mold through the top portion and is allowed to solidify. In general, the gel polymerization process begins once the gel is introduced into the mold. Care is taken to avoid introduction of air bubbles. Often a layer of water is poured on top of the mixture to prevent entry of oxygen during polymerization. After solidification, the plate assembly is removed from the casting stand and, if the gel is to be stored for a period of time, the open ends of the mold are sealed or stored in contact with a gel buffer system.

Other apparatus and methods have been disclosed in for the casting of gel molds. For example, U.S. Pat. No. 4,954,236 discloses an apparatus and method for gel casting and electrophoresis in a single enclosure without the need for a casting stand. Like many of the gel molds of the prior art, such molds experience the swelling difficulties discussed below.

Acrylamide gels tend to swell beginning shortly after the gels are polymerized. This swelling results from relaxation of the acrylamide polymer and is accompanied by an uptake of water. The swelling of the gel tends to occur gradually over a period of two to four weeks because water passes slowly through sealed molds into the gel. In general, the amount of swelling increases with increasing monomer concentration and decreasing cross-linker concentration. For example a gel comprising 14% T and 2.5% C frequently demonstrates an increase in volume of approximately 15–20%, if removed from the mold and soaked in aqueous buffer.

When polyacrylamide gels swell in a confined space they exert strong forces upon their container and upon other regions of the gel. Current gel molds allow the swelling gel to distort the gel mold. This distortion occurs mostly along the central vertical axis of the mold. The bonds between the plates and the spacers along the edge of the mold exert a constricting force on the gel. The force is strongest near the spacer itself and gradually diminishes towards the central axis of the plate. Therefore, expansion is most prevalent along the central mold axis, the farthest distance from the spacers of the mold.

In addition to deforming the mold itself, when gels swell in rigid plastic molds, the uneven forces prevent the gel from swelling uniformly. The pore size gradually becomes smaller as one progresses from the center vertical axis to the spacer at the edge of the mold.

The net result of the distortion of the mold and the variation in pore size is that gels demonstrate a phenomenon known in the art as a "smile." A smile occurs when a gel runs faster in the center lanes where the pore size is larger compared to the side lanes where the pore size is smaller. The smile effect makes it difficult, if not impossible, to obtain a normal pattern of migrating bands when the electrophoresis process is conducted. Since correlations of size depend on straightness across the gel, this aging effect of gel storage affects the gel data quality.

A second problem with current plastic gel molds is their poor conduction of heat. Heat transfer is important in electrophoresis for two reasons. First, polyacrylamide gels are cast by polymerizing acrylamide with a cross-linker in the presence of initiators. This process generates heat. If the heat is not removed, outgassing can result causing the formation of air bubbles in the gel. Usually, the polymerization rates are reduced in order to keep temperature rise to a minimum. Second, the application of a voltage across the gel during the electrophoresis process also generates heat. If this heat is not dissipated, it can cause distortion in the separated protein or poly-nucleic acid bands. This second heat source is a larger problem than the first source described above because it limits the rate at which gels can be run. Increasing temperature reduces resistance, and increases current at a given voltage. Although the net effect is a shorter run, excessive temperature can lead to band broadening. It is preferable to run at a higher voltage and a constant lower temperature.

One advantage to traditional gel mold products that use glass plates of approximately 40 mils (thousandths of an inch) thick is that such thin glass walls have good heat transfer characteristics. Although molds made with glass plates may avoid the heat problems seen in current plastic gel molds and are more rigid than plastic molds, glass plates are disadvantageous in that they are fragile and difficult to assemble, with breakage frequently occurring during shipping and handling of the gel molds, particularly in the case of precast gels. Making the glass thicker increases strength, but reduces heat transfer. Another disadvantage to glass plates is that it is hard to make a leak-proof seal between the glass and the spacer that is still easy to open for gel removal.

Some attempts at making all-film gel cassettes have been made. Although an all-film cassette might solve some gel distortion effects caused by gel swelling it introduces other problems. This form of gel packaging has generally been unsuccessful because the absence of a frame results in inadequate support for the gel. All-film gel molds are difficult to handle, fill and transport. If the film is allowed to flex significantly it often separates from the gel and forms an air space between the film and the gel. This air space causes distortions in the analytes run during the electrophoresis process. Also, even if the gel can be safely handled, it often has to be provided with some form of external support during use. Affixing the gel to the support can itself distort the gel.

It would, therefore, be desirable to provide an electrophoresis gel mold that minimized the effect of gel swelling upon electrophoresis results.

It would also be desirable to provide a plastic electrophoresis gel mold that allowed for efficient temperature control of the gel during electrophoresis.

It would further be desirable to provide a plastic electrophoresis gel mold that was resistant to mechanical damage to the mold or the gel.

It would still further be desirable to provide a plastic electrophoresis gel mold that was simple and inexpensive to manufacture.

SUMMARY OF THE INVENTION

It is an object of this invention to provide an electrophoresis gel mold that minimizes the effect of gel swelling upon electrophoresis results.

It is also an object of this invention to provide a plastic electrophoresis gel mold that allows for efficient temperature control of the gel during electrophoresis.

It is a further object of this invention to provide a plastic electrophoresis gel mold that is resistant to mechanical damage to the mold or the gel.

It is a still further object of this invention to provide a plastic electrophoresis gel mold that is simple and inexpensive to manufacture.

In accordance with this invention, applicants describe an improved electrophoresis gel mold which comprises electrically non-conductive plastic film supported with a rigid plastic frame. The above and other objects and advantages of the present invention will be apparent upon consideration of the drawing and the detailed description of the invention.

DETAILED DESCRIPTION OF THE INVENTION

The present invention relates to an improved electrophoresis gel mold which comprises electrically non-conductive plastic film supported with a rigid plastic frame. In one embodiment of the invention, two rectangular films are supported by a pair of rigid rectangular plastic frames which are separated and held together by spacers which separate the frames at a predetermined thickness and are disposed along three sides of the frame. In a preferred embodiment of the invention, the mold is formed from two injection molded rigid plastic elements to each of which is bonded a plastic film. In another embodiment the plastic films are formed integral with the frame such that the film and frame form a continuous piece of plastic material such that no gluing or other means of attaching the film to the frame is necessary.

Figure 1:
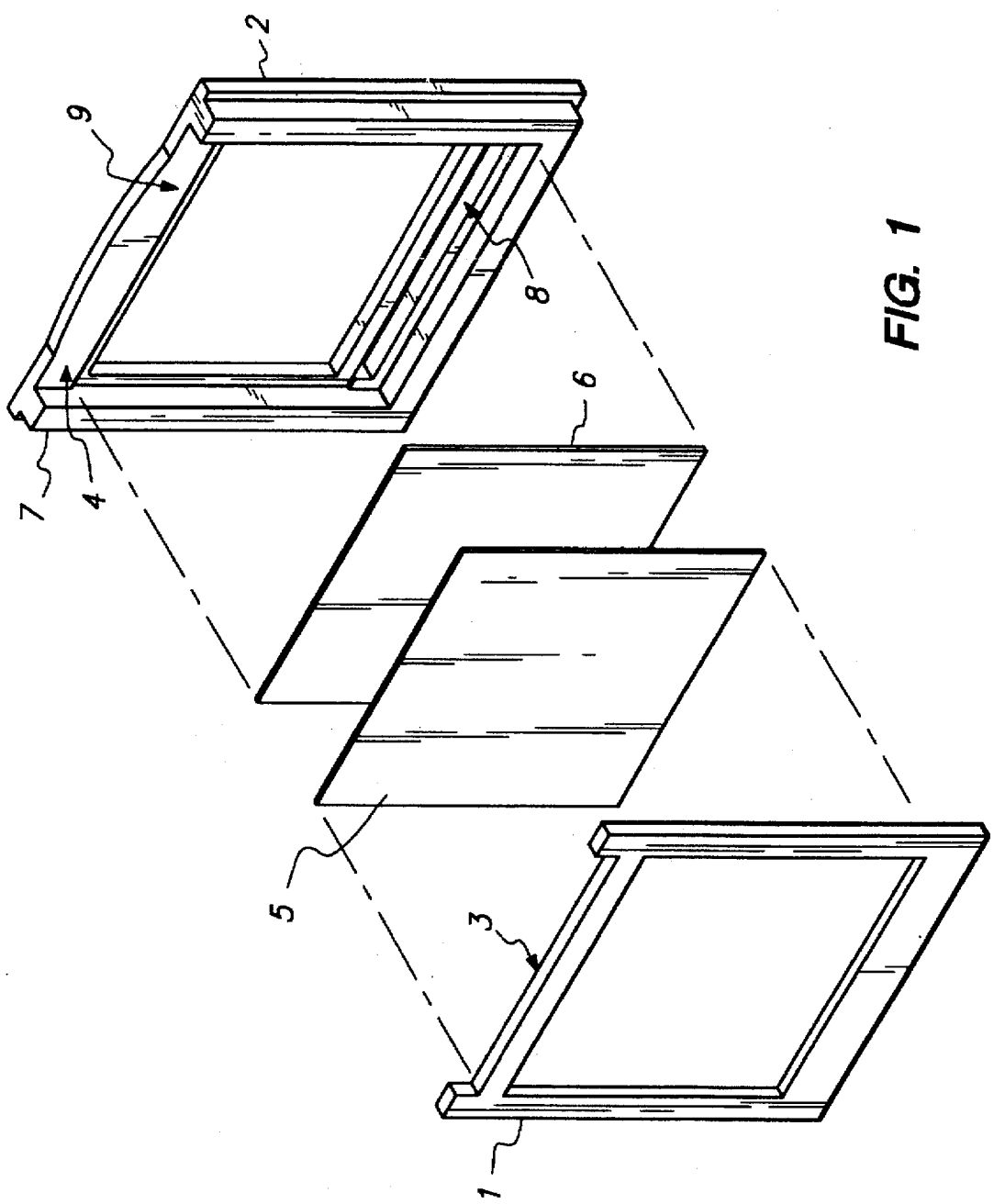
FIG. 1 is a perspective view of an embodiment of a gel mold of the present invention.

Referring to FIG. 1 the gel mold comprises two rigid plastic frames 1 and 2. The plates can be formed by a process such as injection molding. Many different plastics are suitable for forming these plates. Suitable plastics for forming electrophoresis gel molds include polymers such as polyethylene terephthalate, polyvinyl chloride, polycarbonate, polymethyl-methacrylate, polystyrene, polyethylene, polypropylene and cellulose acetates or any of their various co-polymers. It is desirable that the plastic in at least portions of the mold be sufficiently rigid to support the mold.

Referring to FIG. 1, plastic frames 1 and 2 are shown having interior faces 3 and 4 respectively. Frame 2 is also shown to have a U-shaped raised spacer 7 which provides the contact with frame 1 and spaces the interior face 3 of frame 2 from the interior face 4 of frame 1. The height of the raised spacer 7 determines the thickness of the cavity to be formed when the mold is assembled. The spacer can be formed as a protruding surface from either or both of the frames of the cassette. The spacer can also be a separate piece which is permanently secured or bonded to each of the frames by means of ultrasonic welding, gluing, or other means known in the art.

Referring to FIG. 1, affixed to the interior faces of frames 1 and 2 are two plastic films 5 and 6. Films 5 and 6 are bonded at their edges to the interior faces of frames 1 and 2. When the two frames are joined, the films define a slab shaped cavity which is sealed by the raised spacer 7 except for the slot 8 at the lower end of frame 2 and the top opening 9 between frames 1 and 2. The bond between each of the frames of the cassette is leak proof. The bond is also easily broken in order to separate the assembly after the gel has been processed. During preparation of a gel, the slot 8 in frame 2 is sealed. The gel mold is held vertically and gel-forming mixture is poured through the top opening 9 into the cavity between films 5 and 6.

Suitable materials for the manufacture of the plastic film include polymers such as polyethylene terephthalate, polyvinyl chloride, polycarbonate, polymethyl-methacrylate, polystyrene, polyethylene, polypropylene and cellulose acetates or any of their various co-polymers. To be suitable for use in this invention a film must be sufficiently flexible to allow the gel expansion described below. Typically the films should be less than 20 mils thick. Applicants have found that it is preferable to use films less than 10 mils thick. It is also desirable that the film be transparent and colorless so that the progress of the tracking dye through the gel can be easily monitored.

When preparing polyacrylamide gels, the surfaces in contact with the gel during polymerization are preferably provided with an oxygen barrier that reduces diffusion of oxygen from the surface of the plastic films into the gel during that process. A suitable oxygen barrier for an electrophoresis gel is disclosed in applicants copending patent application, Ser. No. 08/242,615, entitled Coated Plastic Mold For Electrophoresis Gel which is incorporated herein by reference. Coatings comprising inorganic oxides such as oxides of silicon are readily applied to plastic films to provide good oxygen barrier layers. Other coatings or treatments that reduce the permeability of the plastic films to oxygen may also be effective. An advantage of the use of film as portion of a gel mold support is that plastic films are more easily and inexpensively provided with oxygen barrier coatings than individual plastic components.

Figure 2:
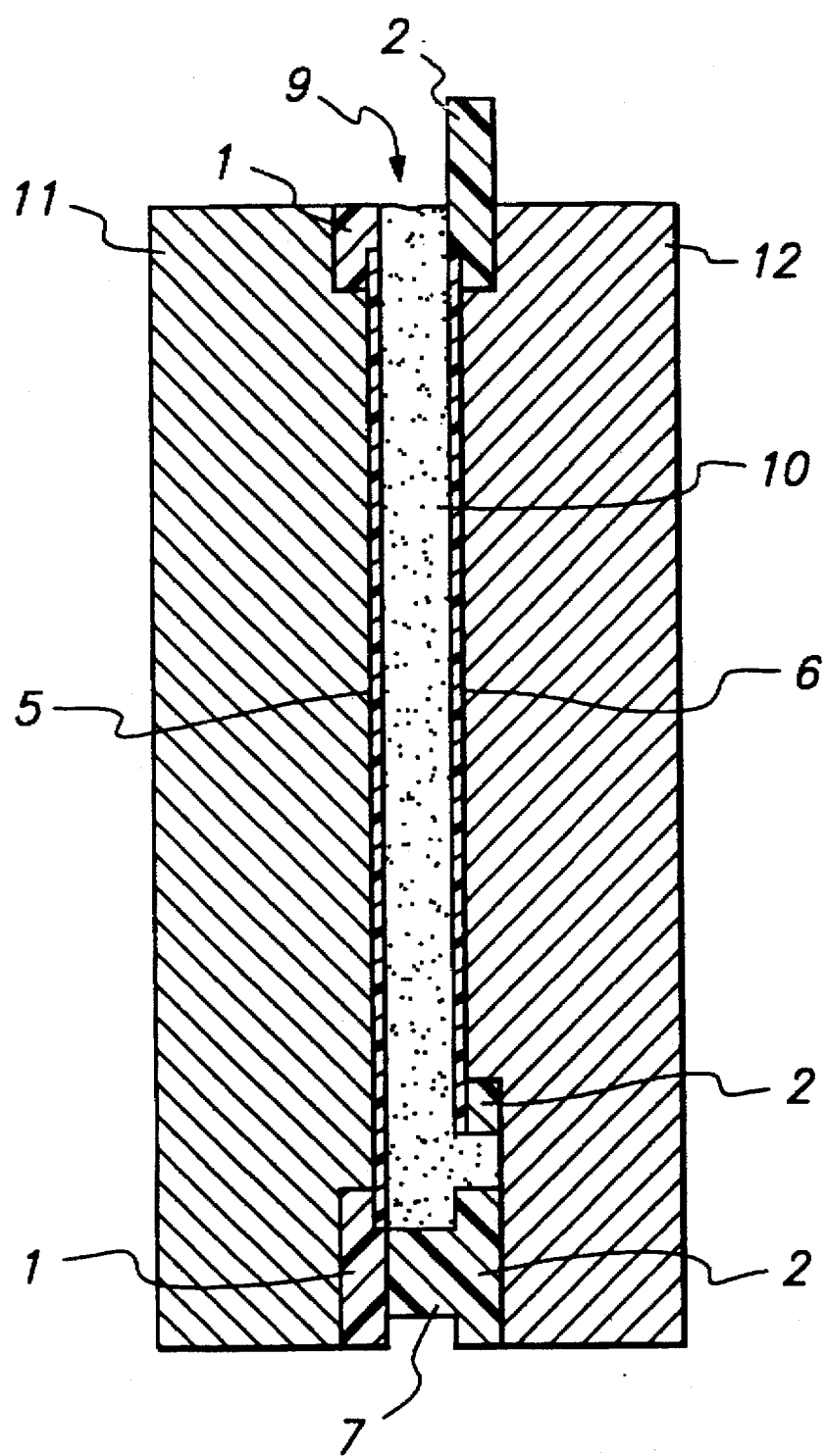
FIG. 2 is a cross-sectional view of the gel mold of FIG. 1 containing an electrophoresis gel and illustrating support elements used during pouring of the gel.

Referring to FIG. 2, a cross section of the coated mold of FIG. 1 is shown during polymerization of an electrophoresis gel 10. The films 5 and 6 are shown affixed to interior faces 3 and 4 of plates 1 and 2. Support elements 11 and 12 of a casting fixture are shown. During the polymerization process, these support elements contact the exterior of films 5 and 6 and maintain the spacing between the films. The cross section is not drawn to scale as a range of thicknesses are possible for the frame and film.

The mold described above avoids the problems discussed above such as gel smiling and other forms of distortion common to gel molds with rigid walls. In the present invention, the film can flex independently across most of the gel surface and can therefore conform to changes in gel thickness. The only area where the film is not able to flex is the area immediately adjacent to the spacer to which the film is attached. The dimensions of this area, which extends outwardly from the edge of the frame toward the central axis, varies and depends upon the flexibility of the film used which is a function of the thickness and type of film material used. Typically, the area is 1 to 3 millimeters from the spacer.

The mold described above also solves the problem of poor heat transfer commonly found in plastic gel molds. The thin films provide much less resistance to heat transfer than is found with thick plastic walls. This allows the gel to be kept at a lower temperature during electrophoresis.

Another advantage of the present invention in precast systems results from the fact that the mold in precast systems are disposed of after a single use. Accordingly, because a smaller volume of plastic is required for a mold using film than for a mold having a solid plastic wall, the film-in-frame design of the present invention results in a significant cost savings in the amount of plastic used to manufacture the mold. Thick plastic gel molds use a lot of plastic, 50 to 60 grams each. The film-in-frame design reduces plastic to about 20 grams. When multiplied by thousands of pre-cast gels used each day, the amount of plastic saved is enormous. Also, the waste that results when the mold is disposed of is also reduced significantly.

Unlike electrophoresis molds made entirely of film, the integrity of the electrophoresis gel in the present invention is maintained by the presence of the supporting frame. This invention solves the support problem of an all-film cassette by having a frame around the perimeter of the film to maintain the shape of the gel and gel mold. The frame serves to prevent distortion of the gel by preventing the gel mold itself from flexing in any direction. This rigidity provided by the frame also helps to prevent the entry of bubbles in the gel or the formation of gaps between the gel and the film which can result if the electrophoresis gel is allowed to bend. Moreover, the area where the comb is inserted (also the upper buffer contact point) and the lower buffer contact point are surrounded and kept in place by the frame.

An alternative embodiment of a plastic gel mold within the scope of this invention could comprise one thick plastic or glass plate and one film supported by a frame as described above. The plastic plate would be fixed to frame to form the mold and allow for gel polymerization. In a second alternative embodiment of a plastic gel mold according to the present invention, films 5 and 6 are formed integral with the frames 1 and 2. Many other configurations of gel molds are possible; each has in common a thin plastic film defining some portion of the cavity enclosing the gel and a rigid supporting frame. The use of the thin plastic film as a portion of the gel mold provides the advantages of improved heat transfer, uniform pressure over the gel surface and reduced material use described above.

The following examples illustrate the advantages of the gel molds of the present invention when compared to prior designs.

EXAMPLES

A gel was cast in a rigid frame and flexible film—rigid frame gel mold, as disclosed and claimed herein, discussed in the examples below. The gel was prepared in either this mold or in a 1.0 mm rigid plastic cassette (NOVEX, San Diego, Calif.) according to the following procedure.

Tris (tris-hydroxy-methyl-amino-methane) and tricine were purchased from Research Organics (Cleveland, Ohio). All other chemicals were either "ultrapure" or "electrophoresis grade" from standard sources. The lower slot on the gel mold was covered with electrical tape (3M, Minneapolis, Minn.). To prepare the separating gel, the stock solutions were blended with ultrapure water to a final concentration of 18% T/2.5% C, or 20% T/1.3% C, with 1.0M Tris-Cl pH 8.45, 3% (w/v) glycerol, and 0.2 ul/ml TEMED. After degassing, 2.1 ul/ml of a 10% solution of APS was added and the solution was immediately poured into a cassette. The stacking gel was prepared in the same fashion as the separating gel, except that the final concentration obtained was 4% T, glycerol was omitted, the TEMED concentration was increased to 1.1 ul/ml and APS increased to 10.4 ul/ml. The stacking gel was carefully poured into the cassette immediately after the separating solution. A ten-well comb, molded from polycarbonate (NOVEX, San Diego, Calif.) was inserted into the top opening, to form the wells and protect the top surface of the gel from contact with air. Polymerization was allowed to proceed for at least 60 minutes at room temperature.

Running buffer consisted of 0.1M Tris base, 0.1M Tricine, 0.1% SDS at pH 8.3. Samples containing a set of protein standards and various concentrations of Tris HCl, glycerol, and Coomassie Blue G tracking dye were heated for 15 minutes at 70° C. before application. Bovine serum albumin (BSA), lysozyme, and CNBr-digested myoglobin fragments were included in the standard. The sample volume was 5 ul in all cases.

Example 1

Gels were cast as described above at 20% T/1.3% C in 1.0 mm rigid plastic cassettes (NOVEX, San Diego, Calif.). The thickness of the gels plus gel mold was measured at various points around the gel mold surface. Samples were separated on some gels 2 hours after polymerization by running at 125 V constant for approximately 1.5 hours until the dye front reached the bottom of the gel. Other gels had their comb and tape removed and placed in the 1× gel buffer at room temperature. They were measured again and run similarly 5 days later.

The protein bands on these gels after staining with Coomassie R250 ran straight when the gels were fresh. However, after storing for 5 days, there was marked upward bending of the bands in the outer lanes. Sharp, well-formed bands were otherwise observed. These gel molds showed no significant change in thickness near the spacers, and approximately a 4 mils increase near the middle (equivalent to a 10% change in gel thickness which was 1 mm or 40 mils when cast). The gels, when removed from the cassette and placed in water, swelled approximately 30% in width.

Example 2

Gels similar to example 1 were cast in gel molds comprising a rigid frame molded from SAN. QLF-coated 0.5 mil PET film (Airco, Fairfield, Calif.) was laminated to a 4 mil polystyrene film so that the SiOx layer was exposed. This laminate in turn was bonded to the frame using Dymax 181m UV-set adhesive (Dymax, Torrington, Conn.). The frames were assembled with the same adhesive so that the SiOx layer was on the inside of the gel mold. Casting was performed with the aid of a casting fixture as shown in FIG. 2 that maintained parallel walls during filling and polymerization. Measurements, separations, and storage conditions were identical to example 1.

On storage, these gels swelled visibly with the lower percentage stack clearly distinct from the higher percentage separating gel, which appeared very uniform. Thickness measurements revealed a consistent swelling across the gel of approximately 10 mils (equivalent to a 25% change in the gel thickness). The only restriction to swelling was within about 120 mils of the frame. No significant change in protein band straightness was seen after running fresh gels or those stored for 5 days. These gels also swelled about 30% in width when removed from the gel mold and placed in water.

Because the gels ran much cooler, the protein bands in these gels migrated at about 85% of the rate of those from gels in example 1.

Example 3

Gels were cast as described above at 18% T/2.5% C in the 1.0 mm rigid plastic cassettes. No samples were applied to the gel. They were run at either 8 or 16 watts constant power in a mini-cell (NOVEX, San Diego, Calif.) with 1× gel buffer used as the running buffer. The running buffer was chilled to 16° C. by recirculating the buffer through a coil in a temperature-controlled water bath (Fotodyne, Hartland, Wis.). After 30 minutes, the gel temperatures were measured. The gel temperatures were found to be 22° C. for the gel run at 8 watts, and 25° C. for the gel run at 16 watts.

Example 4

Gels similar to example 3 were cast in molds as described in example 2. The gels were run as in example 3 with the running buffer again cooled to 16° C. After 30 minutes, the gel temperatures were measured. The gel temperatures were found to be 19° C. for gels run at both 8 watts and 16 watts.

Example 1 illustrates how rigid gel molds do not permit the gel to swell uniformly across its width. Example 2 illustrates how, in comparison, the gel mold of the present invention allows uniform expansion of the gel and thus minimizes variation in gel thickness and pore size. Thus, the gel molds of the present invention, by permitting uniform swelling across the gel to very near the edges, ensure that bands in all lanes migrate evenly.

The use of a flexible film in the gel mold permits the gel to expand uniformly in thickness as it ages so that it tends to maintain uniform separation characteristics over its life. This uniformity is particularly important in pre-cast gels, which are usually manufactured, then stored for weeks or months before use. Glass or plastic sheets used to make rigid wall gel molds deform, but not uniformly, causing defects in pre-cast gels over time that otherwise show no chemical breakdown in the polyacrylamide.

Example 3 illustrates the temperature rise in an electrophoresis gel during passage of an electrical current. Example 4 illustrates how gel molds of the present invention allow better heat conduction out of the gel and, therefore, allow the electrophoresis gel to run at a lower temperature. The gel mold of the present invention tends to have heat conductance characteristics equal to or better than typical glass gel molds, and much better than rigid-walled plastic gel molds.

As described above, this invention solves the problem of uneven swelling, brittleness, heat transfer, cost, and leakage of glass and rigid plastic plates by using: (a) thin plastic film which is not brittle, but still maintains good thermal conductivity; (b) plastic injection-molded frames which are rather thick and therefore easy to injection mold; and (c) an all plastic gel mold which can be assembled with heat, ultrasonics, or adhesives making a leak-proof seal that is easy to open.

While the invention has been explained in relation to its preferred embodiments, it is to be understood that various modifications thereof will become apparent to those skilled in the art. The foregoing disclosure is not intended or to be construed to limit the present invention, or to otherwise exclude any such other embodiments, adaptions, variations and equivalent arrangements, the present invention being limited only by the claims appended hereto and the equivalents thereof.

We claim:

1. An electrophoresis gel mold comprising:

two rectangular supports separated by a spacer;

wherein the two supports and the spacer define a cavity for receiving an electrophoresis gel;

wherein at least one of the supports comprises a plastic film connected at its periphery to a rectangular plastic frame;

wherein the rectangular plastic frame comprises a rigid rectangular border defining an aperture;

wherein the aperture has substantially the same area as one entire surface of said cavity for receiving an electrophoresis gel;

wherein the plastic film is connected at its periphery to the plastic frame so as to cover said aperture, so that the plastic film defines substantially one entire surface of said cavity for receiving an electrophoresis gel; and wherein the plastic film is not directly contacted by a rigid sheet.

2. A mold as in claim 1 wherein the film is bonded to the rectangular plastic frame.

3. A mold as in claim 1 wherein the film is formed integral with the rectangular plastic frame.

4. A mold as in claim 1 wherein the plastic film is not more than 20 mils in thickness.

5. A mold as in claim 1 wherein the surface of said plastic film adjacent said cavity for receiving an electrophoresis gel is coated with a layer forming an oxygen barrier.

6. A mold as in claim 5 wherein said oxygen barrier layer comprises an oxide of silicon.

7. A medium for electrophoresis comprising:

an electrophoresis gel sandwiched between two supports;

wherein at least one of the supports comprises a plastic film connected at its periphery to a rectangular plastic frame;

wherein the rectangular plastic frame comprises a rigid border defining an aperture;

wherein the plastic film is connected at its periphery to the plastic frame so as to cover said aperture, so that the plastic film supports substantially one entire surface of said electrophoresis gel; and wherein the plastic film is not directly contacted by a rigid sheet.

8. A medium for electrophoresis as in claim 7 wherein the plastic film is bonded to the rectangular plastic frame.

9. A medium for electrophoresis as in claim 7 wherein the film is formed integral with the rectangular plastic frame.

10. A medium for electrophoresis as in claim 7 wherein the plastic film is not more than 20 mils in thickness.

11. A medium for electrophoresis as in claim 10 wherein the surface of said plastic film adjacent the electrophoresis gel is coated with a layer forming an oxygen barrier.

12. A medium for electrophoresis as in claim 11 wherein said oxygen barrier layer comprises an oxide of silicon.

13. A medium for electrophoresis comprising:

an electrophoresis gel sandwiched between two supports;

wherein at least one of said supports comprises a rectangular piece of plastic film;

wherein said plastic film is connected along each edge to a plastic frame;

wherein the plastic frame comprises a rigid border defining an aperture;

wherein the plastic film is connected at its periphery to the plastic frame so as to cover said aperture, so that the Plastic film supports one surface of said electrophoresis gel; and wherein the plastic film is not directly contacted by a rigid sheet.

14. A medium for electrophoresis as in claim 13 wherein said plastic film is formed integral with the plastic frame.

15. A medium for electrophoresis as in claim 13 wherein said plastic film is bonded to the plastic frame.

16. A medium for electrophoresis as in claim 13 wherein the surface of said plastic film adjacent the electrophoresis gel is coated with a layer forming an oxygen barrier.

17. A medium for electrophoresis as in claim 13 wherein said oxygen barrier layer comprises an oxide of silicon.

* * * * *